us008551979B2

United States Patent
Yama et al.

(10) Patent No.: US 8,551,979 B2
(45) Date of Patent: Oct. 8, 2013

(54) NONAQUEOUS PREPARATION FOR PERCUTANEOUS ABSORPTION CONTAINING NONSTEROIDAL ANTI-INFLAMMATORY ANALGESIC

(75) Inventors: Seijirou Yama, Toyama (JP); Naoki Murai, Toyama (JP)

(73) Assignee: Lead Chemical Co., Ltd., Toyama (JP)

( * ) Notice: Subject to any disclaimer, the term of this patent is extended or adjusted under 35 U.S.C. 154(b) by 92 days.

(21) Appl. No.: 11/666,624

(22) PCT Filed: Nov. 5, 2004

(86) PCT No.: PCT/JP2004/016431
§ 371 (c)(1),
(2), (4) Date: Apr. 30, 2007

(87) PCT Pub. No.: WO2006/048939
PCT Pub. Date: May 11, 2006

(65) Prior Publication Data
US 2008/0113010 A1    May 15, 2008

(51) Int. Cl.
*A01N 43/00*    (2006.01)
*A61K 31/33*    (2006.01)

(52) U.S. Cl.
USPC .......................................... 514/183; 424/448

(58) Field of Classification Search
None
See application file for complete search history.

(56) References Cited

U.S. PATENT DOCUMENTS

| 4,740,374 | A | * | 4/1988 | Nakano et al. ............... 424/448 |
| 5,059,626 | A | * | 10/1991 | Park et al. ..................... 514/658 |
| 5,234,957 | A | * | 8/1993 | Mantelle ..................... 514/772.6 |
| 5,478,567 | A | * | 12/1995 | Nakagawa et al. ........... 424/449 |
| 2003/0149383 | A1 | * | 8/2003 | Ikeura et al. ..................... 602/8 |
| 2004/0048755 | A1 | * | 3/2004 | Lopes ........................... 510/111 |

FOREIGN PATENT DOCUMENTS

| EP | 0 947 584 A1 | | 10/1999 |
| EP | 174132 A1 | * | 1/2002 |
| EP | 872247 B1 | * | 6/2003 |
| JP | 59036609 A | * | 2/1984 |
| JP | 59181211 | * | 10/1984 |
| JP | 59181211 A | * | 10/1984 |
| KR | 2000-0024702 | | 5/2000 |

OTHER PUBLICATIONS

Mortazovi et al, "An investigation into the effect of various penetration enhancers on percutaneous absorption of piroxicam", Iranian Journal of Pharmaceutical Research, 2003, pp. 135-140.*
Jan. 25, 2010 Supplementary European Search Report issued in EP 04 82 2361.

* cited by examiner

*Primary Examiner* — Brandon Fetterolf
*Assistant Examiner* — Jean Cornet
(74) *Attorney, Agent, or Firm* — Oliff & Berridge, PLC

(57) ABSTRACT

The present invention relates to nonaqueous preparation for percutaneous absorption prepared by laminating an adhesive layer comprising a nonsteroidal anti-inflammatory analgesic in an alkali metal salt form, and an inorganic acid which is strongly acidic compared with the nonsteroidal anti-inflammatory analgesic in a free form, together with a nonaqueous base, on a support. According to the present invention, drug-releasing characteristics and skin penetration in a nonaqueous preparation for percutaneous absorption can be improved because the addition of an inorganic acid in a nonaqueous base containing a drug in an alkali metal salt form leads to an improvement in the solubility of the drug in the base, and a good partitioning of the drug to skin surface. In addition, as the inorganic acid has no alcoholic hydroxy group in the structure, the inorganic acid does not react with the drug, therefore it causes no lowering in the stability of the drug by esterification.

10 Claims, No Drawings

NONAQUEOUS PREPARATION FOR PERCUTANEOUS ABSORPTION CONTAINING NONSTEROIDAL ANTI-INFLAMMATORY ANALGESIC

TECHNICAL FIELD

The present invention relates to a nonaqueous preparation for percutaneous absorption containing nonsteroidal anti-inflammatory analgesic that is excellent in percutaneous absorption and stability.

BACKGROUND ART

Nonsteroidal anti-inflammatory analgesics do not show severe side-effects as shown in steroidal anti-inflammatory analgesics, and thus are drugs widely used in the clinical practice. However, in case where nonsteroidal anti-inflammatory analgesics are orally administered, they show any inhibition activity against cyclooxygenase being a prostaglandin generating enzyme present in the living bodies, and therefore it is recognized to cause side-effects such as stomach mucosa disorder. In order to reduce such side-effects, preparations absorbed through the skin, that is, transdermal preparations are developed.

Bases for the transdermal preparations are classified into two categories, an aqueous base and a nonaqueous base. The nonaqueous base includes a rubbery base, an acrylic base, silicone and the like. In the meantime, when a drug in a salt form is formulated in a nonaqueous base, the application thereof to the skin does not lead to so large amount of skin penetrated drug as to exert the pharmacological effect because compatibility between the drug and the base is low and drug-releasing characteristics from the base is extremely low. Further, as the drug is not dissolved in the base, there is also a problem that the drug availability is low. In practice, the comparative experiments on drug-releasing characteristics and skin penetration between an drug in a salt form added in a nonaqueous base and an drug in no salt form added in a nonaqueous base confirm that the drug in a salt form is low in releasing characteristics and skin penetration compared with the drug in no salt form.

However, many of the prior arts on transdermal preparation containing anti-inflammatory analgesic as an active ingredient do not distinguish between drugs in no salt form and drugs in a salt form as an active ingredient that is contained in the preparation or may be added in the base, and most of the prior arts only state the name of a drug in a salt form as mere example of anti-inflammatory analgesic. For example, it is reported an anti-inflammatory analgesic plaster prepared by applying a base component comprising at least one nonsteroidal anti-inflammatory analgesic selected from ketoprofen, flurbiprofen, loxoprofen, ketorolac, and the ester derivatives and salts thereof, a solvent comprising both a rosin ester derivative and 1-menthol, a styrene-isoprene-styrene block copolymer as a base polymer, and a softener, on a support made of polyester fabric (see, for example Patent Document 1). The anti-inflammatory analgesic plaster accomplishes an improvement in percutaneous absorption and drug-releasing characteristics, reduction of side-effects such as skin irritation or the like, and simple usability by formulating the above-mentioned base components. However, the document do not distinguish as nonsteroidal anti-inflammatory analgesic, drugs in a salt form from drugs in no salt form, and therefore the plaster is clearly unsuitable for the above-mentioned reasons.

On the other hand, it is also known an anti-inflammatory analgesic plaster prepared by laminating a pressure-sensitive adhesive material layer containing a nonsteroidal anti-inflammatory analgesic in an alkali metal salt form and an organic acid that is strongly acidic compared with the nonsteroidal anti-inflammatory analgesic in a free form, on a flexible support (see, for example Patent Document 2). Since, most of the organic acid have alcoholic hydroxy group, the hydroxy group is reacted with carbonyl group of carboxylic acid on the nonsteroidal anti-inflammatory analgesic represented by loxoprofen sodium to give an ester that causes a problem that the stability of the anti-inflammatory analgesic is lowered.

Patent Document 1: JP Patent No. 2816765 (1998)
Patent Document 2: JP B 7-47535 (1995)

PROBLEMS TO BE SOLVED BY THE INVENTION

The present invention intends to solve the above-mentioned problems, and more concretely an object of the present invention is to provide a nonaqueous preparation for percutaneous absorption containing a drug in a salt form in a nonaqueous base, which is excellent in drug-releasing characteristics and skin penetration, and which prevents lowering in the stability of the drug even when a salt of carboxylic acid such as loxoprofen sodium, diclofenac sodium, or the like is used.

MEANS FOR SOLVING THE PROBLEMS

The present inventors eagerly studied in order to solve the above-mentioned problems, and consequently found that the mixing of a drug in an alkali metal salt form together with an inorganic acid in a nonaqueous base leads to an improvement in solubility of the drug in the nonaqueous base, and a good partitioning of the drug to skin surface, thus an easy penetration even through the horny layer as a barrier layer.

Therefore, the present invention relates to a nonaqueous preparation for percutaneous absorption prepared by laminating an adhesive layer comprising a nonsteroidal anti-inflammatory analgesic in an alkali metal salt form, and an inorganic acid which is strongly acidic compared with the nonsteroidal anti-inflammatory analgesic in a free form, together with a nonaqueous base, on a support.

Preferable embodiments of the present invention relate to
the nonaqueous preparation for percutaneous absorption, wherein the inorganic acid is phosphoric acid;
the nonaqueous preparation for percutaneous absorption, wherein the nonsteroidal anti-inflammatory analgesic is loxoprofen sodium;
the nonaqueous preparation for percutaneous absorption, wherein the nonaqueous base is composed of A-B-A type block copolymer; and
the nonaqueous preparation for percutaneous absorption, wherein the adhesive layer further comprises a plasticizer, a tackifier, a penetration accelerator and/or a stabilizer.

EFFECT OF THE INVENTION

According to the present invention, drug-releasing characteristics and skin penetration in a nonaqueous preparation for percutaneous absorption can be improved because the addition of an inorganic acid in a nonaqueous base containing a drug in an alkali metal salt form leads to an improvement in the solubility of the drug in the base, and an easy transport of the drug to skin surface. In addition, as the inorganic acid has no alcoholic hydroxy group in the structure, the inorganic acid does not react with the drug, therefore it causes no lowering in the stability of the drug by esterification.

BEST MODE FOR CARRYING OUT THE INVENTION

The adhesive layer of the nonaqueous preparation for percutaneous absorption according to the present invention comprises a nonsteroidal anti-inflammatory analgesic in an alkali metal salt form, and an inorganic acid, in a nonaqueous base.

The adhesive component that can be used for the nonaqueous base includes rubbery adhesives, acrylic adhesives, silicone adhesives and the like. From the viewpoint of properties, the cost for production, ease of quality design, and reproducibility and the like, it is preferable to use rubbery adhesives.

Rubber components in the rubbery adhesives include natural rubber, polyisoprene, styrene-isoprene-styrene block copolymer, styrene-butadiene-styrene block copolymer, styrene butadiene rubber and polyisobutylene. The rubber component may be used singly or in a combination of two or more. In particular, styrene-isoprene-styrene block copolymer and styrene-butadiene-styrene block copolymer that are A-B-A type block copolymer are preferable.

As the nonsteroidal anti-inflammatory analgesic in an alkali metal salt form, medicinally acceptable salts of loxoprofen and diclofenac are particularly preferable.

The inorganic acid is not specifically limited so long as it is strongly acidic compared with the nonsteroidal anti-inflammatory analgesic in a free form, and medicinally acceptable inorganic acids such as phosphoric acid, hydrochloric acid, sulfuric acid and the like can be used. Phosphoric acid being a non-volatile acid is particularly preferable. The inorganic acid may be used singly or in a combination of two or more. Although the blending quantity of the inorganic acid is not specifically limited, based on the total amount of the compounds contained in the adhesive layer, 0.01 to 20% by weight is preferable, 0.1 to 10% by weight is more preferable and 0.2 to 5% by weight is particularly preferable.

The adhesive layer in the nonaqueous base component of the present invention can further comprise a plasticizer, a tackifier, a penetration accelerator and/or a stabilizer.

The plasticizer is not specifically limited, and includes for example petroleum oil (paraffin process oil, naphthene process oil, aromatic process oil, etc.), squalane, squalene, vegetable oil (olive oil, camellia oil, castor oil, tall oil, earthnut oil, etc.), silicone oil, dibasic acid ester (dibutyl phthalate, dioctyl phthalate, etc.), liquid rubber (polybutene, liquid isoprene rubber, etc.), liquid fatty ester (isopropyl myristate, hexyl laurate, diethyl sebacate, diisopropyl sebacate, etc.), diethylene glycol, polyethylene glycol, glycol salicylate, propylene glycol, dipropylene glycol, triacetin, triethyl citrate, crotamiton, and the like. Among these plasticizers, liquid paraffin, isopropyl myristate, diethyl sebacate and hexyl laurate are preferable, and liquid paraffin is particularly preferable. In addition, the plasticizer may be used singly or in a combination of two or more. Although the blending quantity of the plasticizer is not specifically limited, based on the total amount of the compounds contained in the adhesive layer, 5 to 70% by weight is preferable, 10 to 60% by weight is more preferable and 10 to 50% by weight is particularly preferable. In case where the blending quantity of the plasticizer is less than 5% by weight, the effect of improvement in cohesion of the adhesive layer by the blending of the plasticizer tends to become insufficient. On the other hand, in case where it is more than 70% by weight, the skin penetration of drug tends to become insufficient.

The tackifier is not specifically limited, and includes for example rosin derivatives (rosin, glycerin ester of rosin, hydrogenated rosin, glycerin ester of hydrogenated rosin, pentaerythritol ester of rosin, etc.), alicyclic saturated hydrocarbon resin (Arkon P100 manufactured by Arakawa Chemical Industries, Ltd., etc.), aliphatic hydrocarbon resin (Quintone B-170 manufactured by Zeon Corporation, etc.), terpene resin (Clearon P-125 manufactured by Yasuhara Chemical Co., Ltd., etc.), maleic acid resin, and the like, and particularly glycerin ester of hydrogenated rosin, aliphatic hydrocarbon resin and terpene resin are preferable. The tackifier may be used singly or in a combination of two or more. Although the blending quantity of the tackifier is not specifically limited, based on the total amount of the compounds contained in the adhesive layer, 5 to 70% by weight is preferable, 5 to 60% by weight is more preferable and 10 to 50% by weight is particularly preferable. In case where the blending quantity of the tackifier is less than 5% by weight, the effect of improvement in adhesion of the adhesive layer by the blending of the tackifier tends to become insufficient. On the other hand, in case where it is more than 70% by weight, the skin irritation on peeling off of the nonaqueous preparation for percutaneous absorption tends to be increased.

The penetration accelerator is not specifically limited so long as it is a compound on which penetration accelerating action in skin is conventionally recognized, and includes specifically $C_{6-20}$ fatty acids, aliphatic alcohols, aliphatic esters, amides or ethers, aromatic organic acids, aromatic alcohols, aromatic organic acid esters or ethers, and the like. These compounds may be either saturated or unsaturated ones, and straight, branched or cyclic ones. Further, lactates, acetates, monoterpene compounds, sesquiterpene compounds, azone, azone derivatives, glycerin fatty acid esters, propylene glycol fatty acid esters, sorbitan fatty acid esters (Span type), polysorbate compounds (Tween type), polyethylene glycol fatty acid esters, polyoxyethylene hydrogenated castor oil compounds (HCO type), polyoxyethylene alkyl ethers, sucrose fatty acid esters, vegetable oil and the like can be used as the penetration accelerator.

Among the penetration accelerators, the followings are preferable: caprylic acid, capric acid, caproic acid, lauric acid, myristic acid, palmitic acid, stearic acid, isostearic acid, oleic acid, linoleic acid, linolenic acid, lauryl alcohol, myristyl alcohol, oleyl alcohol, isostearyl alcohol, cetyl alcohol, methyl laurate, hexyl laurate, lauric diethanol amide, isopropyl myristate, myristyl myristate, octyldodecyl myristate, cetyl palmitate, salicylic acid, methyl salicylate, salicylic ethylene glycol, cinnamic acid, methyl cinnamate, cresol, cetyl lactate, lauryl lactate, ethyl acetate, propyl acetate, geraniol, thymol, eugenol, terpineol, l-menthol, borneol, d-limonene, isoeugenol, isoborneol, nerol, dl-camphor, glycerin monocaprylate, glycerin monocaprylate, glycerin monolaurate, glycerin monooleate, sorbitan monolaurate, sucrose monolaurate, polysorbate 20, propylene glycol, propylene glycol monolaurate, polyethylene glycol monolaurate, polyethylene glycol monostearate, polyoxyethylene lauryl ether, HCO-60, pyrothiodecane and olive oil, and the followings are more preferable: lauryl alcohol, myristyl alcohol, isostearyl alcohol, lauric diethanol amide, glycerin monocaprylate, glycerin monocaprate, glycerin monooleate, sorbitan monolaurate, propylene glycol monolaurate, polyoxyethylene lauryl ether and pyrothiodecane.

The penetration accelerator may be used singly or in a combination of two or more. Although the blending quantity of the penetration accelerator is not specifically limited, based on the total amount of the compounds contained in the adhesive layer, 0.01 to 20% by weight is preferable, 0.05 to 10% by weight is more preferable and 0.1 to 5% by weight is particularly preferable. In case where the blending quantity of the penetration accelerator is less than 0.01% by weight, the effect of improvement in skin penetration of drug by the blending of the penetration accelerator tends to become insufficient. On the other hand, in case where it is more than 20% by weight, the skin irritation such as edema, etc. tends to be increased, and further adhesion to skin tends to be lowered.

The adhesive layer in the present invention can contain a stabilizer such as antioxidants, UV absorbers and the like, and further fillers, crosslinking agents, antiseptic agents and the like, if necessary.

The antioxidants are preferably tocopherol and ester derivatives thereof, ascorbic acid, ascorbic stearate, nordihydroguaia retinoic acid, dibutyl hydroxytoluene (BHT) and butyl hydroxyanisole; the UV absorbers are preferably p-aminibenzoic acid derivatives, anthranilic acid derivatives, salicylic acid derivatives, coumarin derivatives, amino acid type compounds, imidazoline derivatives, pyrimidine derivatives and dioxane derivatives. The fillers are preferably calcium carbonate, magnesium carbonate, silicates (aluminum silicate, magnesium silicate, etc.), silicic acid, barium sulfate, calcium sulfate, calcium zincate, zinc oxide and titanium oxide; the crosslinking agents are preferably amino resins, phenol resins, epoxy resins, alkyd resins, thermoset resins such as unsaturated polyester or the like, isocyanate compounds, blocked isocyanate compounds, organic crosslinking agents, inorganic crosslinking agents such as metals or metal compounds; the antiseptic agents are preferably ethyl paraoxybenzoate, propyl paraoxybenzoate and butyl paraoxybenzoate.

Although the blending quantity of each of the above-mentioned antioxidants, UV absorbers, fillers, crosslinking agents and antiseptic agents is not specifically limited, the total amount of the antioxidants, UV absorbers, fillers, crosslinking agents and antiseptic agents is preferably 0 to 10% by weight, more preferably 0 to 5% by weight, and particularly preferably 0 to 2% by weight based on the total amount of the compounds contained in the adhesive layer.

The nonaqueous preparation for percutaneous absorption of the present invention is prepared by spreading and laminating the adhesive layer formulated as mentioned above on a support. The support is not specifically limited so long as it can support the adhesive layer, and stretch or non-stretch supports can be used. Such supports are concretely ones made of fabric, unwoven fabric, polyurethane, polyester, polyvinyl acetate, polyvinylidene chloride, polyethylene, polyethylene terephthalate, aluminum sheet or the like, or composite material thereof.

Although the thickness of the support is not specifically limited, it is preferable that the thickness ranges from 5 to 1000 µm. In case where the thickness of the support is less than 5 µm, handling ease for putting the nonaqueous preparation for percutaneous absorption on tends to be lowered, on the other hand, in case where it is more than 1000 µm, the cutting of the support or the adhesive layer tends to become difficult, and thus production ease tends to be lowered.

Although the thickness of the adhesive layer in the nonaqueous preparation for percutaneous absorption of the present invention is not specifically limited, it is preferable that the thickness ranges from 20 to 200 µm. In case where the thickness of the adhesive layer is less than 20 µm, skin penetration of drug tends to become insufficient, on the other hand, in case where it is more than 200 µm, phenomenon that the adhesive layer is adhered to skin and remain thereon after putting on (adhesive deposit) easily tends to occur. In addition, from the viewpoint of the maintenance of adhesiveness and the property of following skin, it is preferable that the weight of the adhesive in the nonaqueous preparation for percutaneous absorption is 40 g/m$^2$ or more.

In the production of the nonaqueous preparation for percutaneous absorption of the present invention, the method for laminating an adhesive layer on a support is not specifically limited, and for example the nonaqueous preparation for percutaneous absorption of the present invention can be prepared by heat-melting a mixture of components constituting the adhesive layer and applying it on a support.

In addition, in case where the nonaqueous preparation for percutaneous absorption of the present invention is provided with an exfoliate paper, the nonaqueous preparation for percutaneous absorption of the present invention can be prepared by applying a heat-melted mixture of components constituting the adhesive layer on an exfoliate paper, and laminating it on a support in a state where the applied surface faces the support, or by applying a heat-melted mixture on a support, and laminating it on an exfoliate paper in a state where the applied surface faces the exfoliate paper. The nonaqueous preparation for percutaneous absorption of the present invention can be also prepared by using an application solution prepared by dissolving the mixture in a solvent such as toluene, hexane, ethyl acetate or the like, instead of heat-melting the mixture.

Although the exfoliate paper is not specifically limited, specifically films of polyester such as polyethylene terephthalate or the like, polyvinyl chloride, polyvinylidene chloride, laminated films of high-quality paper and polyolefin, and so on can be used. The process of the face of the exfoliate paper which is contact with the adhesive layer with silicone increases handling ease on peeling off and thus is preferable.

Hereinafter, the present invention will be described more specifically based on the Examples to which the present invention is not limited. In addition, hereinafter unless otherwise stated, "%" means "% by mass".

EXAMPLE 1

A nonaqueous preparation for percutaneous absorption of the present invention was produced from the following components:

| | |
|---|---:|
| Styrene isoprene styrene block copolymer (trade name: Kraton D-1107) | 20% |
| Polyisobutylene (manufactured by Exxon Chemical Company) | 5% |
| Alicyclic saturated hydrocarbon resin (trade name: Arkon P-100) | 30% |
| Dibutyl hydroxytoluene | 0.5% |
| Liquid paraffin | 30% |
| Crotamiton | 2% |
| Isopropyl myristate | 2% |
| Diisopropyl adipate | 2% |
| Phosphoric acid | 0.5% |
| l-Menthol | 3% |
| Loxoprofen sodium | 5% |

Components other than a drug, l-menthol and an inorganic acid were melted and kneaded at 120 to 160° C., and then the inorganic acid, the drug and l-menthol were added, and the resulting mixture was spread on a PET film, and a polyester fabric (PET) was laminated thereon, and cut in a prescribed size to obtain a nonaqueous preparation for percutaneous absorption of the present invention.

EXAMPLE 2

A nonaqueous preparation for percutaneous absorption of the present invention was produced in the following formulation according to the production process of Example 1:

| | |
|---|---|
| Styrene isoprene styrene block copolymer (trade name: Kraton D-1107) | 22.5% |
| Polyisobutylene (manufactured by Exxon Chemical Company) | 7.5% |
| Rosin glycerin ester (trade name: Pinecrystal KE-311) | 10% |
| Dibutyl hydroxytoluene | 0.5% |
| Liquid paraffin | 47.5% |
| Phosphoric acid | 1% |
| l-Menthol | 3% |
| Loxoprofen sodium | 5% |

EXAMPLE 3

A nonaqueous preparation for percutaneous absorption of the present invention was produced from the following formulation according to the production process of Example 1:

| | |
|---|---|
| Styrene isoprene styrene block copolymer (trade name: Kraton D-1107) | 20% |
| Polyisobutylene (manufactured by Exxon Chemical Company) | 5% |
| Alicyclic saturated hydrocarbon resin (trade name: Arkon P-100) | 30% |
| Dibutyl hydroxytoluene | 0.5% |
| Liquid paraffin | 34.5% |
| Crotamiton | 1% |
| Isopropyl myristate | 2% |
| Phosphoric acid | 1% |
| l-Menthol | 3% |
| Loxoprofen sodium | 3% |

EXAMPLE 4

A nonaqueous preparation for percutaneous absorption of the present invention was produced according to the formulation and the production process quite similar to those of Example 3 except that phosphoric acid was replaced with hydrochloric acid.

EXAMPLE 5

A nonaqueous preparation for percutaneous absorption of the present invention was produced according to the formulation and the production process quite similar to those of Example 3 except that phosphoric acid was replaced with sulfuric acid.

EXAMPLE 6

A nonaqueous preparation for percutaneous absorption of the present invention was produced according to the formulation and the production process quite similar to those of Example 3 except that loxoprofen sodium was replaced with diclofenac sodium.

EXAMPLE 7

A nonaqueous preparation for percutaneous absorption of the present invention was produced according to the formulation and the production process quite similar to those of Example 4 except that loxoprofen sodium was replaced with diclofenac sodium.

EXAMPLE 8

A nonaqueous preparation for percutaneous absorption of the present invention was produced according to the formulation and the production process quite similar to those of Example 5 except that loxoprofen sodium was replaced with diclofenac sodium.

COMPARATIVE EXAMPLE 1

A nonaqueous preparation for percutaneous absorption for comparison was produced from the following formulation according to the production process of Example 1:

| | |
|---|---|
| Styrene isoprene styrene block copolymer (trade name: Kraton D-1107) | 20% |
| Polyisobutylene (manufactured by Exxon Chemical Company) | 5% |
| Alicyclic saturated hydrocarbon resin (trade name: Arkon P-100) | 30% |
| Dibutyl hydroxytoluene | 0.5% |
| Liquid paraffin | 30.5% |
| Crotamiton | 2% |
| Isopropyl myristate | 2% |
| Isopropyl adipate | 2% |
| l-Menthol | 3% |
| Loxoprofen | 5% |

COMPARATIVE EXAMPLE 2

A nonaqueous preparation for percutaneous absorption for comparison was produced from the following formulation according to the production process of Example 1:

| | |
|---|---|
| Styrene isoprene styrene block copolymer (trade name: Kraton D-1107) | 22.5% |
| Polyisobutylene (manufactured by Exxon Chemical Company) | 5% |
| Rosin glycerin ester (trade name: Pinecrystal KE-311) | 10% |
| Dibutyl hydroxytoluene | 0.5% |
| Liquid paraffin | 52.5% |
| l-Menthol | 3% |
| Lactic acid | 4% |
| Loxoprofen sodium | 5% |

COMPARATIVE EXAMPLE 3

A nonaqueous preparation for percutaneous absorption for comparison was produced from the following formulation according to the production process of Example 1:

| | |
|---|---|
| Styrene isoprene styrene block copolymer (trade name: Kraton D-1107) | 20% |
| Polyisobutylene (manufactured by Exxon Chemical Company) | 5% |
| Alicyclic saturated hydrocarbon resin (trade name: Arkon P-100) | 18% |
| Dibutyl hydroxytoluene | 0.5% |
| Liquid paraffin | 42.5% |
| Crotamiton | 2% |
| Macrogol 400 | 1% |
| l-Menthol | 3% |
| Tartaric acid | 1% |
| Loxoprofen sodium | 2% |

COMPARATIVE EXAMPLE 4

A nonaqueous preparation for percutaneous absorption for comparison was produced according to the formulation and the production process quite similar to those of Example 3 except that phosphoric acid was not used.

COMPARATIVE EXAMPLE 5

A nonaqueous preparation for percutaneous absorption for comparison was produced according to the formulation and the production process quite similar to those of Example 6 except that phosphoric acid was not used.

COMPARATIVE EXAMPLE 6

A nonaqueous preparation for percutaneous absorption for comparison was produced according to the following formulation described in Patent Document 1.

| | |
|---|---|
| Styrene isoprene styrene block copolymer (trade name: Kraton D-1107) | 20% |
| Hydrogenated rosin ester (trade name: Estergum H) | 21% |
| Dibutyl hydroxytoluene | 2% |
| Liquid paraffin | 45% |
| l-Menthol | 9% |
| Loxoprofen sodium | 3% |

TEST EXAMPLE 1

Stability Test

The nonaqueous preparation for percutaneous absorption of Example 1 and Comparative Examples 1 and 2 were stored at 60° C. for 3 weeks, and drug content after storage was measured and compared with drug content before storage. The results are shown in Table below.

TABLE

Percent remaining of drugs after storage at 60° C. for 3 weeks

| | Percent remaining (%) |
|---|---|
| Example 1 | 96.5 |
| Comparative Example 1 | 86.9 |
| Comparative Example 2 | 92.3 |

From the results shown in Table, it was confirmed that the nonaqueous preparation for percutaneous absorption of the present invention had a high percent remaining. On the contrary, it was confirmed that the stability of the preparation in which loxoprofen in no salt form was used was lowered. In addition, in the preparation in which lactic acid was added as an organic acid, a large amount of decomposed products derived from lactic acid was detected from the preparation stored at 60° C. for 3 weeks.

TEST EXAMPLE 2

Drug Releasing Test

The nonaqueous preparation for percutaneous absorption of Examples 3 to 7 and Comparative Examples 4 and 5 were subjected to drug releasing test in phosphoric acid buffer of pH 7.4, and percent releasing of drugs from the nonaqueous preparation for percutaneous absorption was determined. The results are shown in Table below.

TABLE

Percent releasing of drugs in phosphoric acid buffer

| | Percent releasing of drugs after 24 hours (%) |
|---|---|
| Example 3 | 80.88 |
| Example 4 | 93.53 |
| Example 5 | 88.96 |
| Example 6 | 32.25 |
| Example 7 | 30.68 |
| Comparative Example 4 | 7.71 |
| Comparative Example 5 | 12.64 |

From the results shown in Table, it became clear that in the nonaqueous preparation for percutaneous absorption of the present invention containing nonsteroidal anti-inflammatory analgesic in a salt form with an alkali metal, the addition of an inorganic acid was essential in order to improve drug releasing characteristics from a base.

TEST EXAMPLE 3

In Vitro Skin Penetration Test with Skin Excised from Rat Abdomen

The nonaqueous preparation for percutaneous absorption of Examples 1 to 3 and Comparative Examples 3, 4 and 6 were subjected to in vitro penetration test using excised skin from rat abdomen. The results are shown in Table below.

TABLE

Drug skin penetration

| | Cumulative penetrated amount for 24 hours (nmol/cm$^2$) |
|---|---|
| Example 1 | 196.0 |
| Example 2 | 392.7 |
| Example 3 | 278.5 |
| Comparative Example 3 | 12.2 |
| Comparative Example 4 | 8.54 |
| Comparative Example 6 | 101.6 |

As shown in Table, it became clear that Examples 1 to 3 were clearly excellent in drug releasing characteristics and percutaneous absorption (cumulative penetration amount) compared with Comparative Examples 3, 4 and 6.

The invention claimed is:

1. A nonaqueous preparation for percutaneous absorption prepared by laminating an adhesive layer comprising a nonsteroidal anti-inflammatory analgesic in an alkali metal salt form, and an inorganic acid which is strongly acidic compared with the nonsteroidal anti-inflammatory analgesic in a free form, together with a nonaqueous base, on a support, wherein:
   the inorganic acid is phosphoric acid and the nonsteroidal anti-inflammatory analgesic is loxoprofen sodium,
   the adhesive layer further comprises a rosin glycerin ester as a tackifier, a liquid paraffin as a plasticizer, and l-menthol as a penetration accelerator, and
   the nonaqueous base is composed of an A-B-A type block copolymer.
2. The nonaqueous preparation for percutaneous absorption according to claim 1, wherein the A-B-A type block copolymer is a styrene-isoprene-styrene block copolymer or styrene-butadiene-styrene block copolymer.

3. The nonaqueous preparation for percutaneous absorption according to claim 1, wherein the adhesive layer further comprises an antioxidant.

4. The nonaqueous preparation for percutaneous absorption according to claim 2, wherein the adhesive layer further comprises an antioxidant.

5. The nonaqueous preparation for percutaneous absorption according to claim 1, wherein the inorganic acid is present in an amount of 0.1 to 10% by weight based on a total weight of the adhesive layer.

6. The nonaqueous preparation for percutaneous absorption according to claim 1, wherein the loxoprofen sodium is present in an amount of 3 to 5% by weight based on a total weight of the adhesive layer.

7. The nonaqueous preparation for percutaneous absorption according to claim 1, wherein the inorganic acid is present in an amount of 0.1 to 10% by weight and the loxoprofen sodium is present in an amount of 3 to 5% by weight, based on a total weight of the adhesive layer.

8. The nonaqueous preparation for percutaneous absorption according to claim 1, wherein the tackifier and the plasticizer are each present in an amount of 5 to 70% by weight.

9. The nonaqueous preparation for percutaneous absorption according to claim 1, wherein the A-B-A type block copolymer is a styrene-isoprene-styrene block copolymer.

10. The nonaqueous preparation for percutaneous absorption according to claim 9, wherein the inorganic acid is present in an amount of 0.1 to 10% by weight and the loxoprofen sodium is present in an amount of 3 to 5% by weight, based on a total weight of the adhesive layer.

* * * * *